United States Patent [19]

Takatani et al.

[11] Patent Number: 4,867,557
[45] Date of Patent: Sep. 19, 1989

[54] REFLECTION TYPE OXIMETER FOR APPLYING LIGHT PULSES TO A BODY TISSUE TO MEASURE OXYGEN SATURATION

[75] Inventors: Setsuo Takatani, Hyogo; Kunio Awau; Masahiko Kanda, both of Osaka, all of Japan

[73] Assignee: Sumitomo Electric Industries, Ltd., Osaka, Japan

[21] Appl. No.: 180,047

[22] Filed: Apr. 11, 1988

[30] Foreign Application Priority Data

Apr. 9, 1987 [JP] Japan .................................. 62-87468

[51] Int. Cl.$^4$ ............................................. G01N 33/49
[52] U.S. Cl. ........................................ 356/41; 128/633
[58] Field of Search ..................... 356/40, 41; 128/633

[56] References Cited

U.S. PATENT DOCUMENTS

| 2,706,927 | 4/1955 | Wood | 356/41 |
| 3,638,610 | 2/1972 | Lyles et al. | 118/636 |
| 4,523,279 | 6/1985 | Sperinde et al. | 356/41 X |

FOREIGN PATENT DOCUMENTS

| 51785 | 4/1977 | Japan . |
| 88778 | 8/1978 | Japan . |
| 160445 | 9/1987 | Japan . |

Primary Examiner—Vincent P. McGraw
Attorney, Agent, or Firm—W. G. Fasse; D. H. Kane, Jr.

[57] ABSTRACT

A reflection type oximeter comprises light emitting diodes (11 to 16) as first to sixth light sources which emit first and second beams of a wavelength involving a change in absorption due to a change an oxygen saturation of hemoglobin in blood of a tissue of a living body, third and fourth beams of another wavelength involving no change in absorption, and fifth and sixth beams of a further wavelength involving a relatively small change in absorption due to changes in a quantity of hemoglobin an oxygen saturation. The beams ae applied to the body tissue and the beams of the first to sixth light sources reflected by the body are received by a light receiving element (17). Intensities of the beams emitted from the light emitting diodes are set to predetermined levels and the intensities of the beams received by the light receiving element are evaluated by a CPU (23). Based on a predetermined function, the quantity of hemoglobin and of the oxygen saturation of the body tissue are evaluated. The resulting values are displayed on a display portion (26) and printed by a printer (27).

12 Claims, 7 Drawing Sheets

| | | | | |
|---|---|---|---|---|
| P1 | −241 | m | −255 |
| P2 | −242 | VL1 | −256 |
| P3 | −243 | VL2 | −257 |
| P4 | −244 | VL3 | −258 |
| P5 | −245 | VL4 | −259 |
| P6 | −246 | VL5 | −260 |
| PO1 | −247 | VL6 | −261 |
| PO2 | −248 | PM1 | −262 |
| PO3 | −249 | PM2 | −263 |
| PO4 | −250 | PM3 | −264 |
| PO5 | −251 | PM4 | −265 |
| PO6 | −252 | PM5 | −266 |
| PMAX | −253 | PM6 | −267 |
| PMIN | −254 | | |

REFLECTION TYPE OXIMETER FOR APPLYING LIGHT PULSES TO A BODY TISSUE TO MEASURE OXYGEN SATURATION

FIELD OF THE INVENTION

The present invention relates to a reflection type oximeter. More particularly, the present invention relates a reflection type oximeter in which light pulses are applied to a tissue of a living body to measure oxygen saturation or the like in an non-invasive manner based on light reflected from said body.

BACKGROUND INFORMATION

A conventional optical oximeter is known as an apparatus for measuring oxygen saturation in arterial blood based on light transmitted through the finger, the ear or the like of a person to be examined, when light is applied thereto.

U.S. Pat. No. 2,706,927 discloses an apparatus for evaluating oxygen saturation based on measured values of absorbance of each of two different wavelengths in two states, i.e., a state in which the ear is pressed and congested and a state in which the pressure on the ear is relieved. The measured value in the congested state is baased on only absorbant components other than the blood and the measured value in the non-pressed state is based on both of the blood and the other absorbant elements. Therefore, the absorbance of only the blood should be indicated by camparing values read or measured in the two states. However, the precision of the measured value would be lowered because all the blood cannot be removed by pressing the ear and because optical connections between the ear and the optical apparatus vary. In addition, the influence of the absorbant components due to differences in color of the skin and the skin thickness, for example, can differ considerably dependent on the respective persons to be examined and, accordingly, it is necessary to effect a calibration for each person or each measured value.

U.S. Pat. No. 3,638,610, discloses how to avoid described defect by utilization of measured values of absorbance based on a plurality of wavelengths of light. Similarly to all conventional apparatuses, the good result obtained by the apparatus of U.S. Pat. No. 3,638,610 depends on an increase of perfusion in the living body examined. For that reason, the perfusion in the living body is made to be as close as possible to the arterial blood as possible. The perfusion can be increased artificially until an accurate result can be obtained. However, such method is often unfavorable or very difficult dependent on the conditions of the person examined.

Japanese Patent Laying-Open Gazette No. 88778/1978 discloses an oximeter having the below described features. Light of one wavelength and light of another wavelength are applied successively to the fingers, the earlobes or other parts of a living body. The known oximeter comprises photodetector means which generates a first electric signal proportional to part of the light of a wavelength absorbed in such part of the body and generates a second electric signal proportional to part of light of another wavelength in that body part. When the heart sends a larger quantity of blood to the artery tissue than during a heart pause, a larger quantity of blood exists in that part of the body and accordingly the lights of the two wavelengths are more attenuated than during the heart pause. Consequently, the first and second electric signals have peaks of the maximum and minimum values in one pulse period of the heart. The difference of the maximum and minimum peak values entirely depends a pulsating current of blood, while the pulse period is not at all influenced by the absorbant component which attenuates light by a given quantity.

However, a measurement is not permitted in a body part where an artery blood current is not obtained or in a body part where a cuvette necessary for detection of transmitted light cannot be attached.

Japanese Patent Laying-Open No. 51785/1977 discloses a reflection type oximeter which can be attached to a part of a living body without a cuvette as is required in the above described examples. However, the oximeter of Japanese Patent Publication 51785/1977 is used in principle for detecting of a pulsation component and accordingly it is impossible to make measurements if the pulsation component is not obtained.

Japanese Patent Laying-Open No. 160445/1984 discloses an oximeter wherein a pulsation component of the artery blood current is detected as a change of a transmitted light component of the light applied to the tissue, whereby an oxygen saturation in the arterial blood is measured. Consequently, the following disadvantages are involved.

Such an oximeter is incapable of making measurements in a part or a state where a pulsation component does not exist. The measured results are only an oxygen saturation degree and a quantity of hemoglobin and the apparatus is incapable of measuring a tissue oxygen saturation including and providing information on venous blood serving as an index representing metabolism of the tissue. Since the oximeter of Japanese Patent Publication 160445/1984 utilizes transmitting and absorbing functions of the mechanism, it can be attached only to a part used as an optical cell. In addition, since a transmission path of light is not clearly known, it is not clear to which part (volume) the detected information pertains. Further, noise occurs due to sway or vibration of the sensor.

SUMMARY OF THE INVENTION

Therefore, it is a primary object of the present invention to provide a reflection type oximeter which can overcome the above described disadvantages and which is capable of evaluating functions of the lung or the heart of a living body or a state of oxygen supplied to the tissue of the body, and capable of continuously monitoring conditions of a patient for a long period.

The present invention performs its operation by the combination of the following features. First and second beams of a wavelength subjected to a change in absorbance due to a change in oxygen saturation of hemoglobin in blood of tissue of a living body, third and fourth beams of another wavelength not subjected to any change in absorbance, and fifth and sixth beams of a further wavelength subjected to a relatively small change in absorbance due to changes in a quantity of hemoglobin and oxygen saturation, are applied to the tissue of the body, and light receiving means receives the first to sixth beams reflected from the tissue of the body. Intensities of the respective outputs of the light receiving means are evaluated and, based on a predetermined function, the quantity of hemoglobin in the tissue is calculated and the result of the calculation is outputted.

Consequently, the present invention makes it possible to avoid various problems encountered in the conventional non-invasive type oximeters, such as the ability of measuring in a body part where a pulsation component does not exist, measurements limited only to oxygen saturation in an artery, noise due to sway or vibration of a sensor, and the ability of measuring without an optical cuvette because of an optical transmission method. Accordingly, the oximeter of the present invention is capable of evaluating lung functions, heart functions, the state of oxygen supplied to tissue, and other data in examinations of anesthesiology, dermatology, pediatrics etc., and is also capable of continuously monitoring conditions of a patient for a long period.

In a preferred embodiment of the present invention, a calibration mode and a measurement mode can be selected and when the calibration mode is selected, a voltage to be applied to light source means is set so that the intensity of light emitted from the light source means is within a predetermined range.

According to the above-mentioned preferred embodiment of the present invention, the intensity of light emitted from the light source means is calibrated prior to measurement and a quantity of hemoglobin in the tissue of the body can be measured more accurately.

In another preferred embodiment of the present invention, assuming that intensities of the first, second, third, fourth, fifth and sixth beams reflected from the tissue are P1, P2, P3, P4, P5 and P6, the quantity of hemoglobin in the tissue is calculated by:

$$C1 [\log (P3/P4)]^2 + C2 \log (P3/P4) + C3$$

where C1, C2 and C3 are correction values.

In addition, in a further preferred embodiment of the present invention, the light source means is formed by first to sixth light sources emitting the first to sixth beams, respectively, and the first, third and fifth light sources are located at positions distant from the center of the light receiving means by a predetermined distance d1, while the second, fourth and sixth light sources are located at positions distant from the center of the light receiving means by a predetermined distance d2, with a relation of d1<d2 being maintained.

In another aspect of the present invention, first and second beams of a wavelength subjected to a change in absorbance due to a change in oxygen saturation of hemoglobin in the blood of the tissue of a living body, third and fourth beams of another wavelength not subjected to any change in absorbance, and fifth and sixth beams of a further wavelength subjected to a relatively small change in absorbance due to a change in oxygen saturation are applied to the tissue of the body and the first to sixth beams relected therefrom are detected, whereby intensities of the respective beams are evaluated and the oxygen saturation of the tissue is evaluated based on a predetermined function.

Consequently, according to this aspect of the invention, it becomes possible to measure the oxygen saturation in a body part not containing a pulsation component, which could not be measured in a conventional apparatus.

These objects and other objects, features, aspects and advantages of the present invention will become more apparent from the following detailed description of the present invention when taken in conjunction with the accompanying drawings.

BRIEF DESCRIPTION OF THE DRAWINGS

FIG. 4 is a diagram showing data stored in a RAM shown in FIG. 1.

FIG. 5 shows a data sample subroutine, FIG. 6 shows a calibration mode, and FIG. 7 shows a measurement mode.

DESCRIPTION OF THE PREFERRED EMBODIMENTS AND OF THE BEST MODE OF THE INVENTION

Figure 2A:
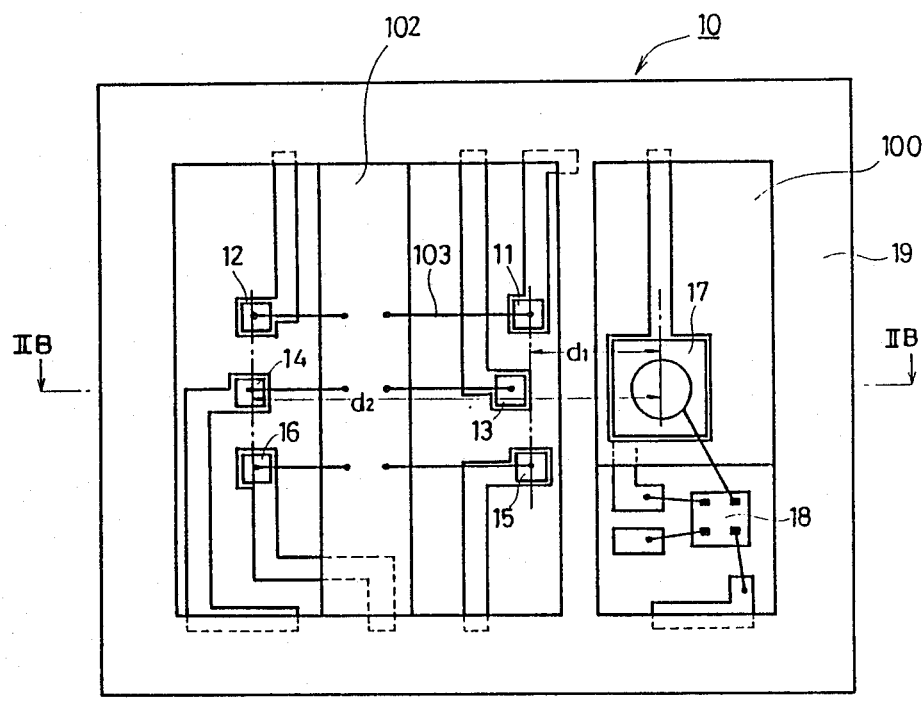
FIG. 2A is a plan view of a sensor portion shown in FIG. 1.
Figure 2B:
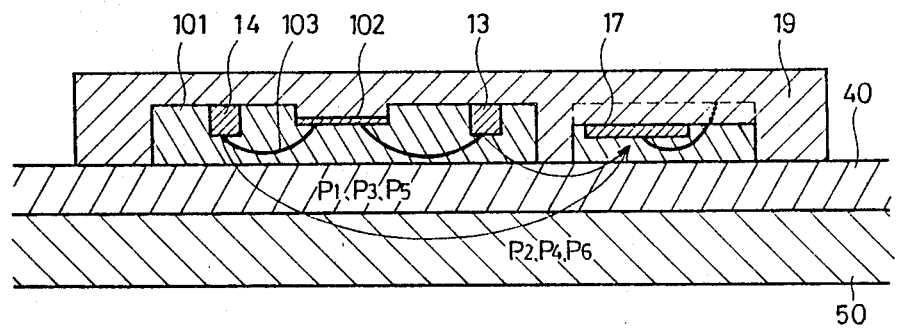
FIG. 2B is a sectional view taken along the line IIB—IIB shown in FIG. 2A.

First referring to FIGS. 2A and 2B, a principle of the present invention will be described. A sensor portion 10 comprises a first light source 11, a second light source 12, a third light source 13, a fourth light source 14, a fifth light source 15, a sixth light source 16, a light receiving element 17, and a preamplifier 18, which are integrally formed as a unitary body disposed on a black ceramic substrate 100. Light emitting diodes are used as the first to sixth light sources 11 to 16. The light emitting diodes 11 and 12 emit light of a wavelength $\lambda1$ (for example, 660 nm), the absorbance of which is considerably changed due to a change in the oxygen saturation in the blood. The light emitting diodes 13 and 14 emit light of a wavelength $\lambda2$ (for example, 805 nm), the absorbance of which undergoes substantially no change due to a change in the oxygen saturation of hemoglobin. The light emitting diodes 15 and 16 emit light of a wavelength $\lambda3$ (for example, 940 nm), the absorbance of which is changed to a relatively small extent due to changes in the oxygen saturation of hemoglobin and the quantity of hemoglobin. The light emitting diodes 11, 13 and 15 are located at positions apart from the center of the light receiving element 17 by a distance d1 and the light emitting diodes 12, 14 and 16 are located at positions apart from the center of the light receiving element 17 by a distance d2, with a relation of d1<d2 being maintained.

There is provided a light interception wall 19 which surrounds the light sources 11 to 16, the light receiving element 17, and the preamplifier 18. The wall 19 separates the light sources 11 to 16 from the light receiving element 17 for preventing an incidence of external light on the light receiving element 17 and to prevent direct application of light from the light sources 1 to 16 to the light receiving element 17. The partition wall which separates the light sources 11 to 16 from the light receiving element 17 has a thickness of 0.5 mm or less for example and a height of about 0.8 mm for example. The wall 19 also prevents resin material 101 (of epoxy, urethane, silicone or the like) introduced onto the light sources 11 to 16 and the light receiving element 17 from flowing outside the wall. A relay electrode 102 is formed between the light sources 11, 13 and 15 and the light sources 12, 14 and 16. The relay electrode 102 comprises a copper film formed on the black ceramic substrate 100 and it distributes electric power supplied from outside the sensor portion 10, to the respective light sources 11 to 16. Electric current is supplied from the relay electrode 102 to the respective light sources 11 to 16 through boding wires 103 and the current is fed back through a printed circuit for example formed on the black ceramic substrate 100.

A detailed description of the transmission of light in the sensor portion 10 thus constructed, is given for example in a document "Photon Diffusion Theory" published by Takaya et al. This theory summarized as follows. The sensor portion 10 is attached to a part of a human body, for example a fingertip, and the light sources 11 to 16 are caused to emit beams successively, so that a plurality of light sources may not emit beams concurrently. The beams emitted by the light sources 11, 13 and 15 near the light receiving element 17 are diffused and reflected in the tissue of the body and reach the light receiving element 17 as shown by arrows in FIG. 2B. Intensities of the beams received in the light receiving element 17 are represented as P1, P3 and P5. The beams emitted by the light sources 12, 14 and 16 distant from the light receiving element 17 are also diffused and reflected in the tissue of the body and reach the light receiving element 17. Intensities of the beams thus received are represented as P2, P4 and P6. The intensities P1, P3 and P5 and the intensities P2, P4 and P6 are obtained through different transmission paths and include different types of information. Let us consider the paths of the reflected beams referring to FIG. 2B. Transmission of the beams is specifically applied according to the above described photon diffusion theory and the intensities of P2, P4 and P6 represent information from a deeper part than the information of the intensities of P1, P3 and P5. Therefore, as shown in FIG. 2B, it is assumed that a region sampled by the intensities of the received beams P1, P3 and P5 is a first layer 40, that a region sampled by the intensities of the received beams P2, P4 and P6 is a second layer 50, and that characteristics given at the time of transmission of the beams in the respective layers are represented as $\alpha 11$ and $\alpha 12$. It is assumed in this case that the characteristics $\alpha 11$ and $\alpha 12$ depend on the transmission, absorption or scattering of the beams from the light sources, hemoglobin existing in the tissue and the like. If intensities of the beams emitted from the light sources 11 and 12 are represented as I1 and I1', respectively, the received light amounts P1 and P2 are represented in the following simplified manner:

$$P1 = I1 \cdot \alpha 11$$

$$P2 = I1' \cdot \alpha 11 \cdot \alpha 12 \quad (1)$$

If a ratio between the intensities of the received beams P1 and P2 is considered, it is represented by the following equation (2).

$$\frac{P2}{P1} = \frac{I1' \cdot \alpha 11}{I1 \cdot \alpha 11 \cdot \alpha 12} \quad (2)$$

If I1=I1', that is, the intensities of the emitted beams are equal, the above stated equation (2) is represented by the following equation (3)

$$P2/P1 = 1/\alpha 12 \quad (3)$$

According to the equation (3), the component of the first layer 40 is removed. This means that only the component of the second layer 50 is detected according to the equation (3). If, for example, the distance d1 (between the light sources 11, 13 and 15 and the light receiving element 17) is set to obtain, as the component of the first layer 40, information of a capillary layer liable to cause disturbance in the bloodstream when it is pressed by the sensor attached and the distance d2 (between the light sources 12, 14 and 16 and the light receiving element 17) is set to obtain, as the component of the second layer 50, information of a bottom of blood hardly subjected to disturbance when it is pressed by the attached sensor, an artifact due to disturbance in the bloodstream, which was a problem to be solved in the prior art, can be removed.

At the same time, skin may be considered as being included in the first layer 40 and the problem of an individual difference such as a difference in the color of the skin, can be also dissolved by applying the above described principle.

Similarly, the above described principle is also applied to the two groups of light sources 13, 14, 15 and 16 having the different wavelengths $\lambda 2$ and $\lambda 3$ of light and the following equations are obtained.

$$\frac{P4}{P3} = \frac{I2' \cdot \alpha 21}{I2 \cdot \alpha 21 \cdot \alpha 22} \quad (4)$$

$$\frac{P6}{P5} = \frac{I3' \cdot \alpha 31}{I3 \cdot \alpha 31 \cdot \alpha 32} \quad (5)$$

In addition, if I2'=I2 and I3'=I3, the following equations are obtained.

$$\frac{P4}{P3} = \frac{1}{\alpha 22}, \frac{P6}{P5} = \frac{1}{\alpha 32} \quad (6)$$

Thus, it is understood that the problem of an artifact influenced by a disturbance in the bloodstream the problem of an individual difference in the skin, can be removed in the same manner as in the case of the wavelength $\lambda 1$.

It is indicated by Takayama et al. for example that the quantity of hemoglobin ($Hb_T$) in the tissue of the living body is obtained in the following manner.

$$Hb_T = C1[\ln(1/R)]^2 + C2[\ln(1/R)] + C3 \quad (7)$$

where R is an intensity of light reflected from the tissue, having a wavelength not causing any change the absorbance due to a change in the oxygen saturation of hemoglobin, and wherein C1, C2 and C3 are coefficients set at the time of calibration. Now, if the principle of the present invention is applied to the above described equation (7), the following equation (8) can be considered.

$$Hb_T = D1 [\log (P3/P4)]^2 + D2 [\log (P3/P4)] + D3 \quad (8)$$

where D1, D2 and D3 are coefficients set at the time of calibration.

From the above-mentioned equation (8), it becomes possible to determine and measure the quantity of hemoglobin ($Hb_T$) in the tissue of the living body by removing the artifact caused by a disturbance in the bloodstream due to the pressure of the sensor attached, or due to the individual difference in the color of the skin.

The oxygen saturation ($S_{O2T}$) of the tissue is expressed by the following equation (9).

$$S_{O2T} = A - B \times \log\left(\frac{P1/P2}{P5/P6}\right) / \log\left(\frac{P3/P4}{P5/P6}\right) \tag{9}$$

where A and B are coefficients set at the time of calibration. In this case also, the theory represented by the above-mentioned equation (6) is applied and it becomes possible to make stable measurements by removing the artifact caused by a disturbance in the bloodstream by pressure of the attached sensor of by the individual difference of the color of the skin.

In the following, the embodiment of the present invention will be described based on the above described principle.

Figure 1:
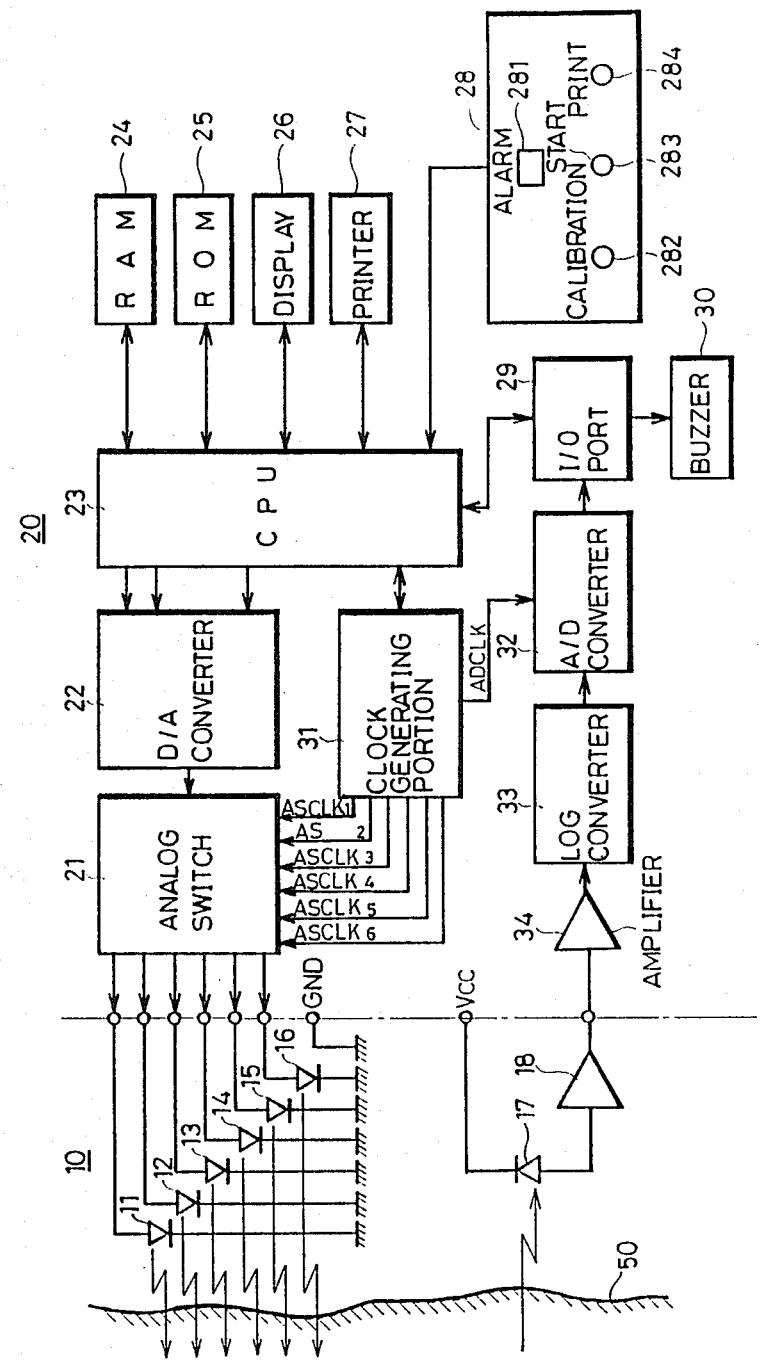
FIG. 1 is a schematic block diagram of an embodiment of the present invention.

Referring to FIG. 1 showing an embodiment of the invention with a reflection type oximeter comprising a sensor portion 10 described above with reference to FIGS. 2A and 2B, and a measurement processing portion 20. The sensor portion 10 comprises the first to sixth light sources 11 to 16, the light receiving element 17 and the preamplifier 18 as described above. The light sources 11 to 16 are driven by the measurement processing portion 20 so that they emit light successively by pulse operation.

The measurement processing portion 20 comprises a central processing unit (CPU) 23 as evaluation means. The CPU 23 supplies, to a D/A converter 22, data for controlling intensities of light pulses emitted from the light sources 11 to 16. The D/A converter 22 converts the data to an analog signal, which is supplied to an analog switch 21. The analog switch 21 comprises six switching elements which are operated by clock signals ASCCKL1, 2, 3, 4, 5 and 6 supplied by a clock generator 31, so that an output of the D/A converter 22 is supplied to the light sources 11 to 16. An output of the light receiving element 17 is supplied to an amplifier 34 through the preamplifier 18, so that it is amplified. An output of the amplification is supplied to a LOG converter 33 so as to be logarithmically converted. An output of the LOG converter 33 is sampled by an A/D converter 32 and outputted as a digital signal. The digital signal is supplied to the CPU 23 through an I/O port 29. The A/D converter 32 receives a clock signal ADCLK from the clock generator 31. The I/O port 29 is connected with a buzzer 30. The buzzer 30 is used to issue an alarm when a result is measured that considerably deviates from a normal value.

Further, the CPU 23 is connected with a RAM 24, a ROM 25, a display portion 26, a printer 27, and an operation portion 28. The RAM 24 stores various data as shown in FIG. 4 as described later. The ROM 25 stores programs based on flowcharts shown in FIGS. 5 to 7. The display portion 26 displays a result of evaluation of the CPU 23 and the printer 27 prints the result of evaluation.

The operation portion 28 includes an alarm LED 281, a calibration key 282, a start key 283 and a print key 284. The alarm LED 281 displays an alarm when a result of calculation has a low reliability. The calibration key 282 is used to set a calibration mode. The start key 283 instructs a start of a measuring mode and the print key 284 instructs a printout of the result of calculation.

Figure 3:
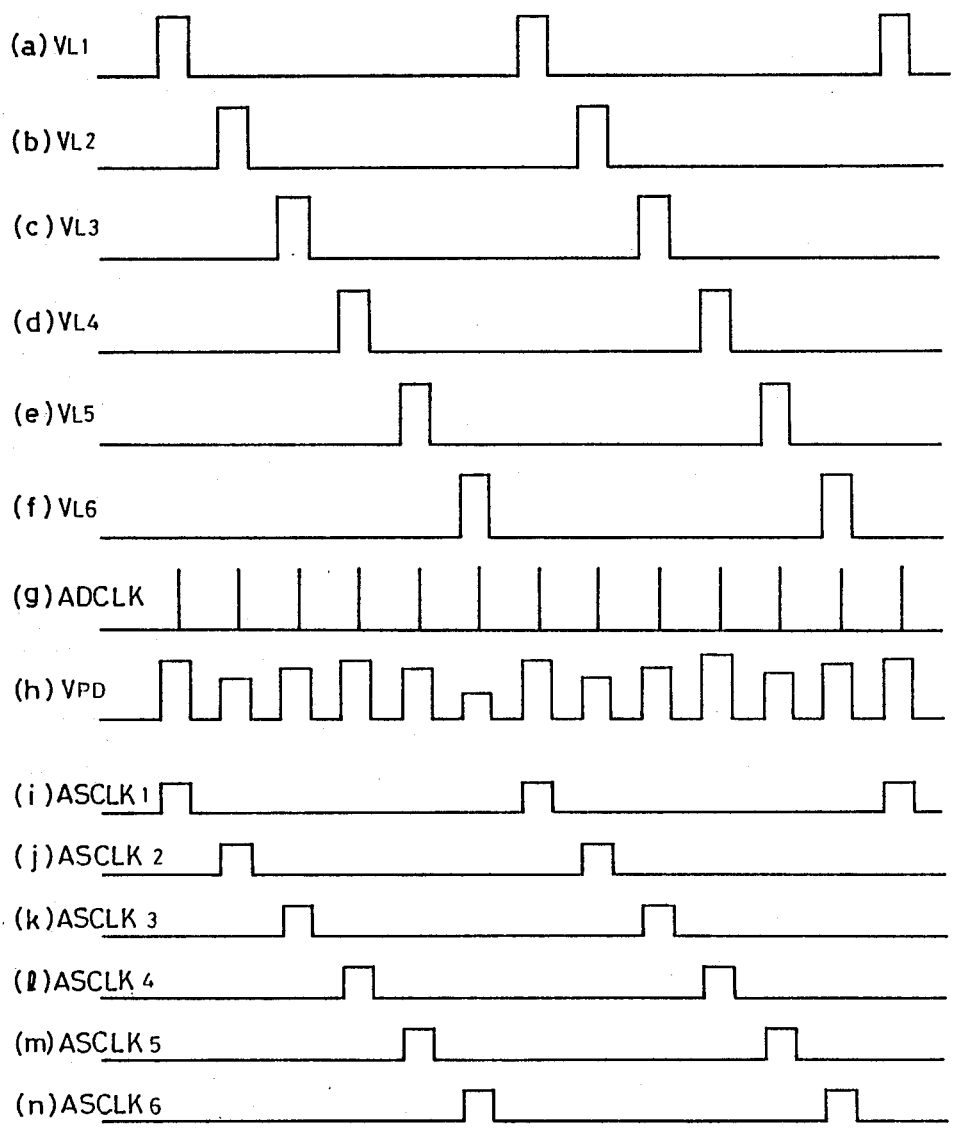
FIG. 3 is a timing chart for detection of the intensities of beams reflected from an object to be measured, said beams having wavelengths $\lambda1$, $\lambda2$ and $\lambda3$.
Figure 5:
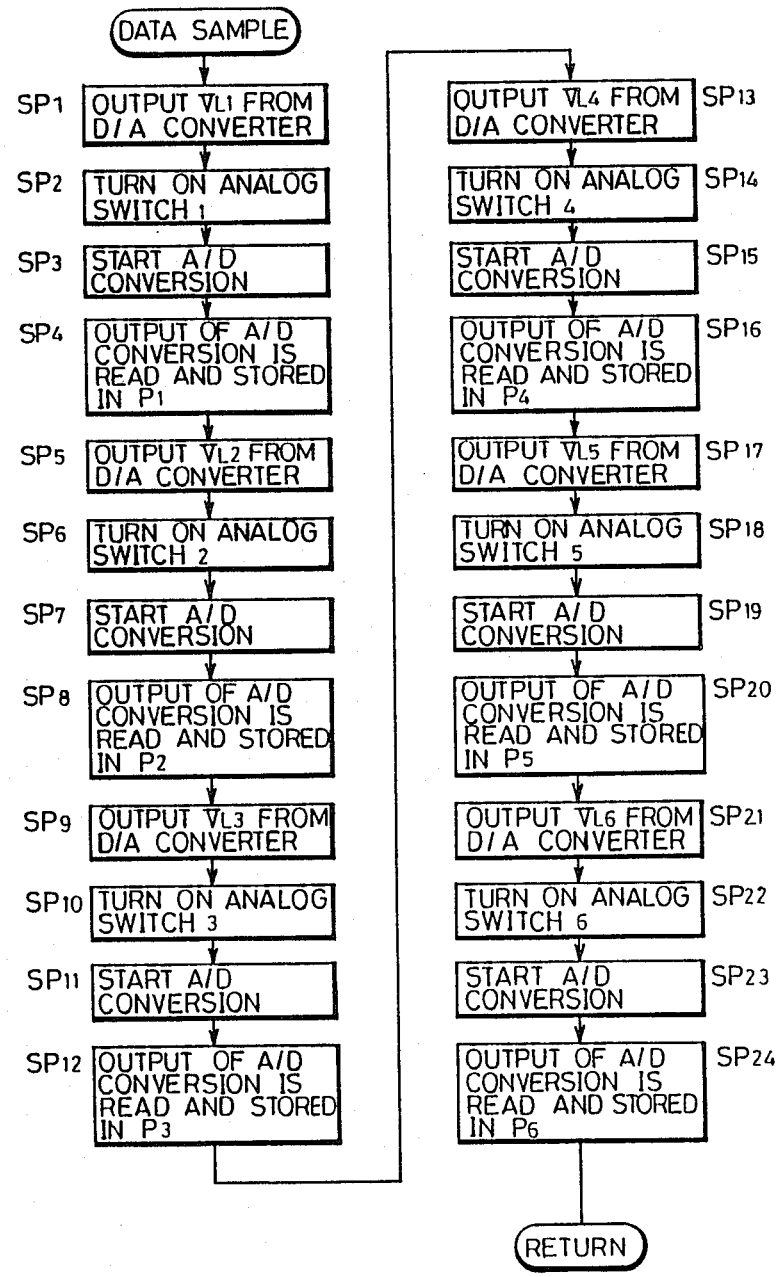
FIGS. 5 to 7 are flowcharts for explaining the actual operation of the embodiment of the present invention. Particularly.
Figure 6:
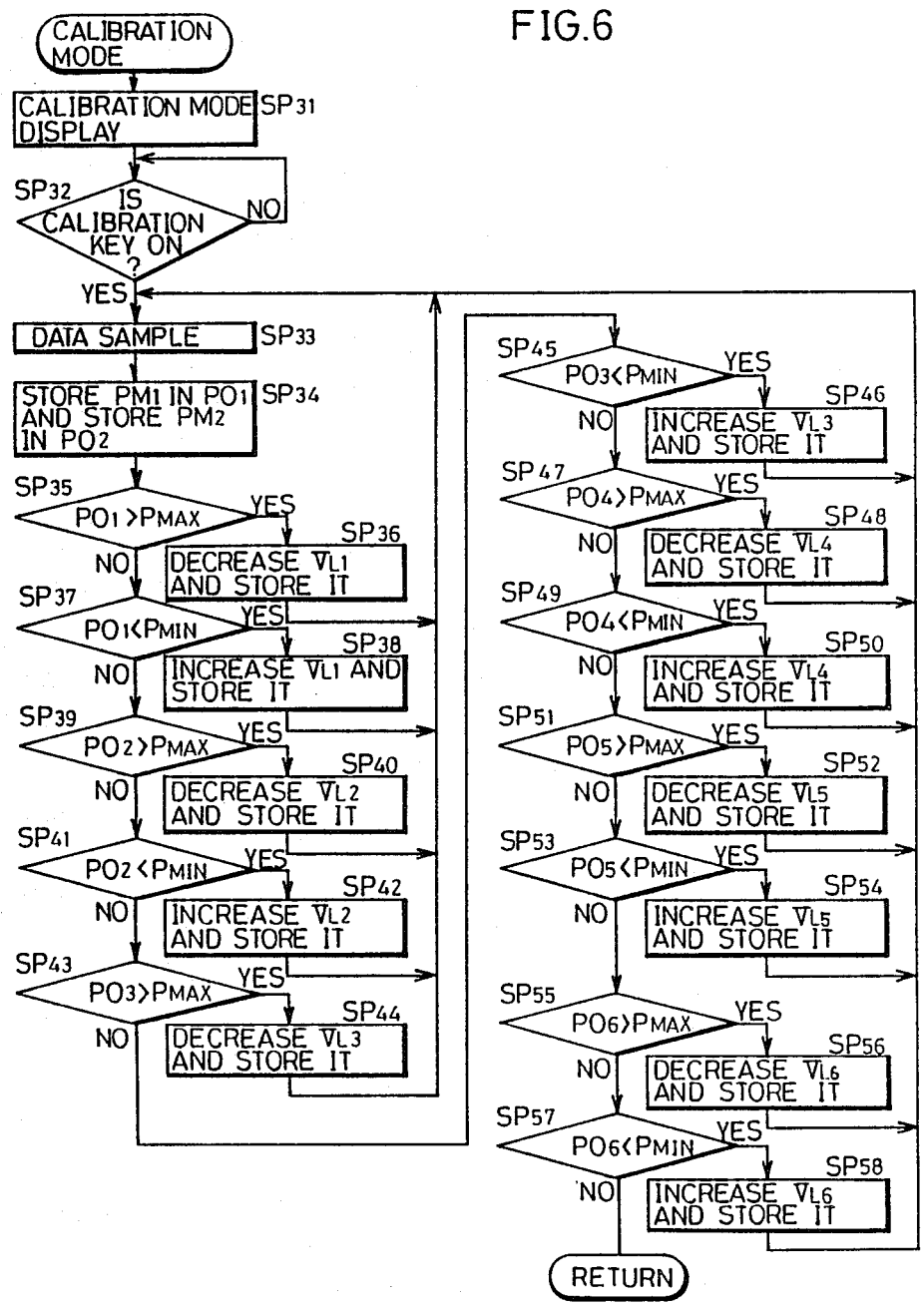
Figure 7:
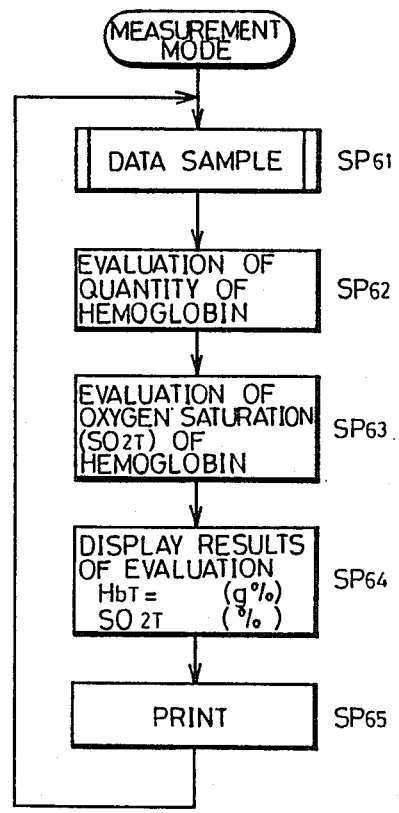

FIG. 3 is a timing chart for detection of intensities of the beams of the wavelengths λ1, λ2 and λ3 transmitted through an object to be measured. FIG. 4 is a diagram showing data stored in the RAM shown in FIG. 1. FIGS. 5 to 7 are flowcharts for explaining an actual operation of the embodiment of the present invention. Particularly, FIG. 5 shows a data sample subroutine; FIG. 6 shows the calibration mode; and FIG. 7 shows the measurement mode.

Referring now to FIGS. 1 to 7, an actual operation of the embodiment will now be described. First, the steps SP1 to SP24 shown in FIG. 5 are procedures sampling the intensities of the beams of the wavelengths λ1, λ2 and λ3 transmitted through the object to be examined and storing the sampled intensities in areas 241 to 246 of the RAM 24.

More specifically, in the step SP1, the CPU 23 reads data of a drive voltage $V_{L1}$ of the first light source 11 stored in a storage area 256 of the RAM 24 shown in FIG. 4 and supplies the data to the D/A converter 22. The D/A converter 22 converts the data of the voltage to an analog signal and supplies it to the analog switch 21. The analog switch 21 receives the clock signal ASCLK1 as shown at (i) of FIG. 3, from the clock generator 31. In the step SP2, the analog switch 21 is turned on in response to the clock signal ASCLK1 and supplies, to the first light source 11, the analog voltage $V_{L1}$ as converted by the D/A converter 22. Then, the first light source 11 emits light of an intensity corresponding to the drive voltage $V_{L1}$ and applies it to the object 50 to be examined.

The emitted light is reflected by the object 50 and is received by the light receiving element 17. The light receiving element 17 converts the received light to an electric signal and supplies it to the amplifier 34 through the preamplifier 18. The amplifier 34 amplifies the signal and supplies it to the LOG converter 33 so that it is logarithmically converted. The logarithmically converted voltage is supplied to the D/A converter 32. The clock signal ADCLK as shown in (g) of FIG. 3 is applied from the clock generator 31 to the A/D converter 32. Accordingly, in the step SP3, the A/D converter 32 converts the analog output of the LOG converter 33 to a digital output based on the clock signal ADCLK. The digital output is supplied to the CPU 23 through the I/O port 29. In the step SP4, the CPU 23 reads the output of the A/D conversion and stores it as P1 in the area 241 of the RAM 24.

Similarly, the CPU 23 reads data of a drive voltage $V_{L2}$ of the second light source shown in (b) of FIG. 3 stored in the area 257 of the RAM 24 and supplies it to the analog switch 21 through the D/A converter 22. The clock signal ASCLK2 as shown in (j) of FIG. 3 is applied by the clock generator 31 to the analog switch 21. Accordingly, in the step SP6, the analog switch 21 is turned on based on the clock signal ASCLK2 to supply the drive voltage $V_{L2}$ to the second light source 12. Then, the second light source 12 emits light of an intensity corresponding to the drive voltage $V_{L2}$ and applies it to the object 50 to be examined. The emitted light of the wavelength λ1 is reflected by the object 50 and is received by the light receiving element 17.

The light receiving element 17 photoelectrically converts the received light and supplies it to the amplifier 34 through the preamplifier 18. The output of the amplifier 34 is logarithmically converted by the LOG converter 33 in the same manner as described above and is supplied to the A/D converter 32. In the step SP7, the A/D converter 32 starts an A/D conversion based on the clock signal ADCLK from the clock generator 31. An output of the A/D conversion is supplied to the CPU 23 through the I/O port 29. In the step SP8, the CPU 23 reads the output of the A/D conversion and stores it as P2 in the area 242 of the RAM 24. Subsequently, the CPU 23 performs the operations steps SP9 to SP24, in which the CPU 23 drives the third to sixth light sources 13 to 16 based on data of the drive voltages $V_{L3}$ to $V_{L6}$ stored in the areas 258 to 261 of the RAM 24 and stores the data as P3 to P6 in the areas 243 to 246, respectively, based on the output of the light receiving element 17.

Now, the calibration mode shown in FIG. 6 will be described. The calibration mode is started when the power supply of the apparatus is turned on or when the operation performed in the measuring mode shown in FIG. 7 as described below is brought to an end. In the step SP31, the CPU 23 displays the calibration mode on the display portion 26. This display serves to indicate that the calibration mode is selected and it also provides an instruction to the operator for attaching the sensor portion 10. According to this instruction, the operator of the apparatus attaches the sensor portion 10 to the object 50 to be examined. Then, in the step SP32, the CPU 23 waits until the calibration key 282 is operated. When the calibration key 282 has been operated, the CPU 23 proceeds to step SP 33 to execute the data sample subroutine shown in FIG. 5.

The CPU 23 measures the data P1 to P6 m times and stores these data. Based on these data stored in the area 255 of the RAM 24 average light data PM1 to PM6 are obtained by averaging the stored data m times. The data PM1 to PM6 are stored in areas 262 to 267 of the RAM 24. Further, the CPU 23 stores the values of PM1 to PM6 in the areas 247 to 252 of the RAM 24 as PO1 to PO6 in the step SP34. Then, the CPU 23 executes the steps SP35 to SP57, in which the drive voltages $V_{L1}$ to $V_{L6}$ applied to the first to sixth light sources 11 to 16, are regulated so that PO1 to PO6 are set between the light data $P_{MAX}$ and $P_{MIN}$ ($P_{MAX} > P_{MIN}$) stored in the areas 253 and 254 of the RAM 24, respectively.

More specifically, in the step SP35, if PO1 is larger than $P_{MAX}$, the CPU proceeds to the step SP36 to set the drive voltage $V_{L1}$ to a small value. Then, the steps SP33 and SP34 are executed again and it is determined in the step SP35 whether PO1 is larger than $P_{MAX}$. If PO1 is not smaller than $P_{MAX}$, the CPU 23 proceeds to the step SP37 to determine whether PO1 is smaller than $P_{MIN}$. If PO1 is smaller than $P_{MIN}$, the value of the drive voltage $V_{L1}$ is increased in step SP38 and then the CPU 23 returns to the above-mentioned step SP33. These operations are repeated to regulate the drive voltage $V_{L1}$ so that PO1 is set between $P_{MAX}$ and $P_{MIN}$.

Subsequently, the operations of steps SP39 to SP58 are executed and the drive voltages $V_{L2}$ to $V_{L6}$ are regulated so that PO2 to PO6 are set between $P_{MAX}$ and $P_{MIN}$. Then, the finally set drive voltages $V_{L1}$ to $V_{L6}$ are stored in the areas 257 to 261 of the RAM 24.

Then, the operator attaches the sensor portion 10 to a part to be examined, for example, a fingertip and operates the start key 283, whereby the CPU 23 proceeds to the measuring mode shown in FIG. 7. More specifically, in step SP61, the above described data sample subroutine shown in FIG. 5 is executed and P1 to P6 based on the light pulses received from the first to sixth light sources 11 to 16, reflected on the part to be examined, are stored in the areas 241 to 246 of the RAM 24. Then, the CPU 23 substitutes P3 and P4 stored in the areas 242 and 245 of the RAM 24 into the above-mentioned equation (8) and evaluates the quantity of hemoglobin $Hb_T$. Further, in step SP63, the CPU 23 substitutes P1, P2, P3, P4, P5 and P6 stored in the areas 241, 243, 244 and 246 of the RAM 24 into the above indicated equation (9) to evaluate the oxygen saturation $S_{O2T}$ of the body tissue. The quantity of hemoglobin $Hb_T$ and the oxygen saturation $S_{O2T}$ of hemoglobin in the body tissue determined by the evaluation operations are displayed on the display portion 26. If the print key 284 is operated in this case, the results of the evaluation $Hb_T$ and $S_{O2T}$ are printed by the printer 27 in the step SP65. The buzzer 30 issues an alarm when the results of measurement become lower than predetermined levels when the patient is being monitored.

As described above, according to the embodiment of the present invention, light pulses of the wavelength the absorbance of which is considerably changed by a change in the oxygen saturation of hemoglobin in the blood of the body tissue and the light pulses the absorbance of which is not changed, and the light pulses the absorbance of which is changed to a small extent by changes in the quantity of hemoglobin and the oxygen saturation are applied at the predetermined levels from the positions near the light receiving portion and the position a little distant therefrom, and the light pulses reflected through the tissue are detected, whereby the oxygen saturation of hemoglobin in the blood of the tissue and the quantity of hemoglobin are evaluated based on the predetermined functions. Consequently, it becomes possible to solve various problems that are present in the conventional non-invasive oximeters, such as the inability of measuring in a part where a pulsation component does not exist, or measurements limited only to the oxygen saturation in an artery, or the occurrence of noise due to sway or vibration of a sensor, or the inability of measuring without an optical cuvette for an optical transmission method. Therefore, the present invention makes it possible to evaluate lung functions, heart functions, conditions of oxygen supplied to the body tissue, and other data in examinations of anesthesiology, dermatology, pediatrics, or the like, and to continuously monitor a patient over a long period of time.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A reflection type oximeter comprising: beam source means including first to sixth beam sources (11 to 16) for emitting first to sixth beams and applying said beams to a living body tissue, wherein first and second beams have a wavelength involving a change in absorbance due to a change in an oxygen saturation of hemoglobin in blood of said body tissue, wherein third and fourth beams have another wavelength involving no change in absorbance, and wherein fifth and sixth beams have a further wavelength involving a relatively small change in absorbance due to changes in a quantity of hemoglobin and in an oxygen saturation, beam receiving means for detecting said first, second, third, fourth, fifth and sixth beams reflected from said tissue, wherein said first, third and fifth beam sources are located at positions distant from a center of said beam receiving means by a predetermined distance d1, and wherein said second, fourth and sixth beam sources are located at positions distant from the center of said beam receiving means by a predetermined distance d2, with a relation of d1<d2 being maintained, evaluation means for evaluating intensities of said first, second, third, fourth, fifth and sixth beams reflected by said body tissue based on an output of said beam receiving means and for evaluating the quantity of hemoglobin in said body tissue based on a predetermined function, and output means (26, 27) for outputting results of the evaluation of said evaluating means.

2. The reflection type oximeter of claim 1, further comprising mode selection means (282, 283) for selecting between a calibration mode wherein a calibration is performed to set the intensities of the beams emitted from said beam source means within predetermined ranges, and a measuring mode wherein a quantity of hemoglobin in said body tissue is evaluated by said evaluation means.

3. The reflection type oximeter of claim 2, further comprising voltage setting means (21, 22) for setting a voltage to be applied to said beam source means in response to selection of the calibration mode by said mode selection means, to cause the intensities of the first to sixth beams emitted from said beam source means to be within said predetermined ranges.

4. The reflection type oximeter of claim 1, further comprising means (23) for calculating an average value of signals of each of said first to sixth beams received by said beam receiving means, said average being calculated a plural number of times, said evaluation means including means for evaluating the quantity of hemoglobin in said body tissue based on said average value and a predetermined function.

5. The reflection type oximeter of claim 1, wherein said evaluation means comprises means for evaluating the quantity of hemoglobin in said body tissue by the expression:

C1[log (P3/P4)]$^2$+C2 log (P3/P4)+C3 wherein P1, P2, P3, P4, P5 and P6 are the intensities of the first, second, third, fourth, fifth and sixth beams reflected from said body tissue, respectively, and C1, C2 and C3 are correction values.

6. A reflection type oximeter comprising: beam source means (11 to 16) including first to sixth beam sources for emitting first to sixth beams and applying said beams to a living body tissue, wherein first and second beams have a wavelength involving a change in absorbance due to a change in an oxygen saturation of hemoglobin in blood of said body tissue, wherein third and fourth beams have another wavelength involving no change in absorbance, and wherein fifth and sixth beams have a further wavelength involving a relatively small change in absorbance due to changes in a quantity of hemoglobin and in an oxygen saturation, beam receiving means (17) for detecting said first, second, third, fourth, fifth and sixth beams reflected from said tissue, wherein said first, third and fifth beam sources are located at positions distant from a center of said beam receiving means by a predetermined distance d1, and wherein said second, fourth and sixth beam sources are located at positions distant from the center of said beam receiving means by a predetermined distance d2, with a relation of d1<d2 being maintained, evaluation means (23) for evaluating intensities of said first, second, third, fourth, fifth and sixth beams reflected by said body tissue based on an output of said beam receiving means and evaluating the oxygen saturation of said body tissue based on a predetermined function, and output means (26, 27) for outputting results of the evaluation by said evaluation means.

7. The reflection type oximeter of claim 6, further comprising mode selection means for selecting between a calibration mode wherein a calibration is performed to set the intensities of the beams emitted from said beam source means within predetermined ranges, and a measuring mode wherein an oxygen saturation of said body tissue is evaluated by said evaluation means.

8. The reflection type oximeter of claim 7, further comprising
voltage setting means (21, 22) for setting a voltage to be applied to said beam source means in response to selection of the calibration mode by said selection means, to cause the intensities of said first to sixth beams emitted from said beam source means to be within said predetermined ranges.

9. The reflection type oximeter of claim 6, further comprising means (23) for calculating an average value of signals of each of said first to sixth beams received by said beam receiving means, said average being calculated a plural number of times, said evaluation means including means (23) for evaluating the oxygen saturation of said tissue based on said average value and said predetermined function.

10. The reflection type oximeter of claim 6, wherein evaluation means comprises means for evaluating the oxygen saturation of said body tissue by the expression:

$$A - B \cdot \log\left(\frac{P1/P2}{P5/P6}\right) / \log\left(\frac{P3/P4}{P5/P6}\right)$$

wherein P1, P2, P3, P4, P5 and P6 are the intensities of the first, second, third, fourth, fifth and sixth beams reflected from said body tissue, respectively, and A and B are correction values.

11. A reflection oximeter comprising: beam source means including first to sixth beam sources for emitting first to sixth beams and applying said beams to a living body tissue, wherein first and second beams have a wavelength involving a change in absorbance due to a change in an oxygen saturation of hemoglobin in blood of said body tissue, wherein third and fourth beams having another wavelength involving no change in absorbance, and wherein fifth and sixth beams have a further wavelength involving a relatively small change in absorbance due to changes in a quantity of hemoglobin and in an oxygen saturation, beam receiving means for detecting said first, second, third, fourth, fifth and sixth beams reflected from said tissue, wherein said first, third and fifth beam sources are located at positions distant from a center of said beam receiving means by a predetermined distance d1, and wherein said second, fourth and sixth beam sources are located at positions distant from the center of said beam receiving means by a predetermined distance d2, with a relation of d1<d2 being maintained, setting means for setting intensities of the beams emitted from said beam source means to predetermined levels, evaluation means for evaluating intensities of said first, second, third, fourth, fifth and sixth beams reflected by said body tissue based on an output of said beam receiving means and for evaluating the quanity of hemoglobin and the oxygen saturation of said body tissue based on a predetermined function, and output means for outputting results of the evaluation by said evaluation means.

12. The reflection type oximeter of claim 11, wherein said intensities of the first, second, third, fourth, fifth and sixth beams reflected from said body tissue are represented as P1, P2, P3, P4, P5 and P6, respectively, wherein said evaluation means evaluate the quantity of hemoglobin of said tissue by the expression:

C1[log (P3/P4)]² + C2 log (P3/P4) + C3 where C1, C2 and C3 are correction values, and wherein said evaluation means evaluates the oxygen saturation of said tissue by the expression:

$$A - B \cdot \log\left(\frac{P1/P2}{P5/P6}\right) / \log\left(\frac{P3/P4}{P5/P6}\right)$$

where A and B are correction values.

* * * * *

UNITED STATES PATENT AND TRADEMARK OFFICE
CERTIFICATE OF CORRECTION

PATENT NO. : 4,867,557
DATED : September 19, 1989
INVENTOR(S) : Setsuo Takatani; Kunio Awazu; Masahiko Kanda It is certified that error appears in the above-identified patent and that said Letters Patent is hereby corrected as shown below:

On the title page:

In [75] replace the second inventor's name to read as follows:
--Kunio Awazu--.

In [57] Abstract, line 4, after "change" insert --in--;
line 10, before "an" insert --and--, replace "ae" by --are--.

Claim 10, line 1 of claim 10, after "wherein" insert --said--.
Claim 11, line 8 of claim 11, replace "having" by --have--;

Signed and Sealed this

Fourteenth Day of August, 1990

Attest:

HARRY F. MANBECK, JR.

*Attesting Officer*  *Commissioner of Patents and Trademarks*